United States Patent [19]

Schloman, Jr.

[11] Patent Number: 4,578,450

[45] Date of Patent: Mar. 25, 1986

[54] ACCELERATOR-MODIFIED ADHESION PROMOTERS FOR RUBBER TO WIRE ADHESION

[75] Inventor: William W. Schloman, Jr., Stow, Ohio

[73] Assignee: The Goodyear Tire & Rubber Company, Akron, Ohio

[21] Appl. No.: 646,342

[22] Filed: Sep. 4, 1984

[51] Int. Cl.$^4$ .............................................. C08G 12/30
[52] U.S. Cl. ..................................... 528/254; 428/65; 428/460; 525/164; 528/258; 528/265
[58] Field of Search ........................ 528/254, 258, 265

[56] References Cited

U.S. PATENT DOCUMENTS 2,263,447 11/1941 Shepard ......................... 528/254 X Primary Examiner—Theodore E. Pertilla
Attorney, Agent, or Firm—M. R. Dion, Sr.

[57] ABSTRACT

There is disclosed the reaction product of an N-(substituted oxymethyl)melamine and a 2-mercaptoarylthiazole and its use as an adhesion promoter to improve rubber to metal wire adhesion.

6 Claims, No Drawings

ACCELERATOR-MODIFIED ADHESION PROMOTERS FOR RUBBER TO WIRE ADHESION

TECHNICAL FIELD

This invention relates to adhesion promoters for improved rubber to wire adhesion and to rubber compositions containing same.

BACKGROUND ART

Various reinforcing materials have been used to increase the strength of rubber articles, including tires, hoses, and the like. Metallic wire, and in particular brass coated steel wire is commonly used as a reinforcement. A primary requirement for effective reinforcement is that the reinforcing material remain tightly bonded to the rubber. Good adhesion is difficult to achieve where, as in the case of a tire, the article is subject to continuous flexing and exposure to high temperatures during use. High initial adhesion may be obtained by providing good mechanical contact between the rubber and the wire during vulcanization but, upon aging and use of the article, the bond strength lessens. To accomplish this, adhesion promoters are commonly used which can increase the level of adhesion between the rubber and the metal. The promoters are commonly added to the rubber compounding recipe prior to vulcanization.

U.S. Pat. No. 3,517,722 to Endter, et al, discloses rubber modified with a resin formed in situ from the reaction of a methylene donor and a methylene acceptor. The donor includes substituted melamine while the acceptor may be m-aminophenol or a resorcinol. Harvey in U.S. Pat. No. 3,992,334 and Thompson in U.S. Pat. No. 4,038,220 also teach the in situ reaction between a substituted melamine and various methylene acceptors to form adhesion promoters for rubber compounds. Bezwada in U.S. Pat. No. 4,539,359. teaches the use of a substituted melamine alone as an adhesion promoter in rubber. Elmer, in U.S. Pat. No. 4,338,263 and Schloman in U.S. Pat. No. 4,436,853 teach the use of the reaction products obtained by reacting a N-(substituted oxymethyl)melamine with a bisphenol and a substituted phenol, respectively, formed outside the rubber compound.

Unfortunately some of these adhesion promoters retard the vulcanization rate. If is therefore desirable that adhesion promoters be developed which have a reduced retardation effect.

DISCLOSURE OF THE INVENTION

In accordance with the practice of the present invention there is provided, as an adhesion promoter, the reaction product of:

(a) an N-(substituted oxymethyl)melamine and (b) a substituted 2-mercaptoarylthiazole accelerator wherein the N-(substituted oxymethyl)melamine has the following structural formula:

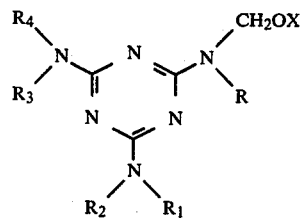

where X is selected from the group consisting of hydrogen and alkyl radicals having 1 to 8, preferably 1 to 6, more preferably 1 to 4 carbon atoms; R, $R_1$, $R_2$, $R_3$, and $R_4$ are selected from the group consisting of hydrogen, alkyl radicals having 1 to 8, preferably 1 to 6, more preferably 1 to 4 carbon atoms, and —$CH_2OX$ where X is as defined above; and the 2-mercaptoarylthiazole accelerator has the following structural formula:

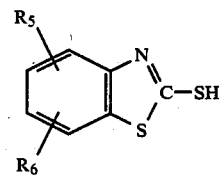

where $R_5$ and $R_6$ are selected from the group consisting of: hydrogen; alkyl radicals having from 1 to 8, preferably 1 to 6, more preferably from 1 to 4 carbon atoms; alkoxy radicals having from 1 to 4, preferably 1 to 3, more preferably 1 to 2 carbon atoms; phenyl radicals either substituted or unsubstituted; amino radical; nitro radical; hydroxy radical; and halo-radicals. R, $R_1$, $R_2$, $R_3$, $R_4$, $R_5$, and $R_6$ may be the same or different.

Representative of, but not limiting, the melamines of the present invention are the following compounds:
hexakis(methoxymethyl)melamine;
N,N′,N″-trimethyl-N,N′,N″-trimethylolmelamine;
hexamethylolmelamine;
N,N-dimethylolmelamine;
N-methylolmelamine;
N,N′,N″-trimethylolmelamine;
N,N′,N″-tri(methoxymethyl)melamine; and
N,N′,N″-tributyl-N,N′,N″-trimethylolmelamine.

A preferred melamine is hexakis(methoxymethyl)-melamine, hereinafter HMMM.

Representative of, but not limiting, the 2-mercaptoarylthiazoles of the present invention are the following compounds:
2-mercaptobenzothiazole, hereinafter MBT;
5-chloro-2-MBT;
4-methyl-2-MBT;
6-nitro-2-MBT;
5-chloro-6-nitro-2-MBT;
6-amido-2-MBT;
4-methoxy-6-chloro-2-MBT;
4-phenyl-2-MBT;
5-ethoxy-2-MBT; and
6-hydroxy-2-MBT.

Preferred is 2-mercaptobenzothiazole.

The reaction products of the present invention can be obtained as condensation products by reacting one or more N-(substituted oxymethyl)melamines and one or more 2-mercaptoarylthiazoles in molar ratios from 0.16 to 10, preferably from 0.25 to 10, at temperatures between 65° C. and 150° C., preferably between 100° C.

and 130° C. The reaction can be accomplished in any atmosphere. For example, the reaction can be accomplished in an inert atmosphere or in the presence of air. The reaction coproduct, alcohol, can best be removed by carrying out the reaction at a reduced pressure or alternatively by such methods as sparging with an inert gas. The order of addition of the reactants is not important. The reaction can be carried out in a non-reactive solvent, however, it is preferred that it be carried out in the absence of a solvent in order to preclude any difficulties in the recovery of the product. The reaction products are generally in the form of resinous liquids or solids.

While HPLC analysis have shown that the reaction product is a multicomponent mixture, the main component of this invention is postulated to have the following structural formula:

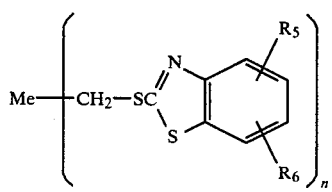

where Me is a melamine structure, n = 1, 2, 3, 4, 5, or 6 and $R_5$ and $R_6$ are as defined above. Representative of compounds which conform to structure III above are those wherein $R_5$, $R_6$ and n are as follows:

| Compound | $R_5$ | $R_6$ | n |
|---|---|---|---|
| 1 | H | H | 1 |
| 2 | Alkyl | Hydroxy | 2 |
| 3 | Phenyl | Nitro | 3 |
| 4 | Chloro | Amino | 4 |

A preferred species of structure III is compound 1.

The reaction products can be used in various rubber compounding recipes to promote the adhesion of metal, usually in the form of a cable or a wire, to the rubber. The specific rubber compounds which may utilize the promoter are limited only to the requirement of being sulfur curable. Thus, recipes may contain natural or synthetic polyisoprene, polybutadiene, styrene-butadiene copolymers, styrene-acrylonitrile copolymers, butyl rubber, halobutyl rubber, the various neoprene rubbers, and/or the ethylene-propylene terpolymers which contain unsaturated hydrocarbon groups. Other rubbers not specifically recited may also be used. The compounding recipes, in addition to containing one or more rubbers, sulfur and the adhesion promoter of the invention, may contain various other well-known compounding ingredients such as antidegradants, carbon black, processing oils and the like, in conventional amounts, as is known in the art of rubber compounding.

The amount of the adhesion promoter used is normally between 1 and 8 parts per 100 parts by weight of the rubber, preferably between 2 and 6 parts per 100 parts by weight of the rubber. The rubber compounds containing the adhesion promoter may be mixed in any conventional manner such as Banbury mixing, mill mixing or combinations thereof. The wire or cable to which rubber adhesion is promoted is generally a steel coated with a copper-containing alloy such as brass or bronze. This type of wire is commonly used in reinforcing layers in the manufacture of tires, power transmission belts, conveyor belts and the like.

The following examples are intended to illustrate the preparation of adhesion promoters and their use in rubber compounds.

EXAMPLE 1

A mixture of 21.4 g of MBT and 50.0 g of HMMM was heated to 120° C. to 130° C. Reaction conditions were maintained while a nitrogen stream was passed through the reaction mixture by means of a sparge tube so as to facilitate the distillation of methanol. After 1.8 g of methanol had been collected, the reaction mixture was cooled, and the product decanted to afford 65.7 g of a tan, resinous solid (Promoter A).

EXAMPLE 2

A mixture of 12.8 g of MBT and 30.0 g of HMMM was heated to 125° C. The pressure in the reactor was reduced below 200 mm Hg by means of a vacuum pump fitted with an in-line cold trap for methanol collection. After 3.8 g of methanol had been collected, the reaction mixture cooled, the reactor pressure returned to atmospheric, and the product decanted to afford 39.0 g of an amber, resinous solid (Promoter B).

It is believed that the main component of Promoter A and Promoter B of examples 1 and 2 has either of the following structures:

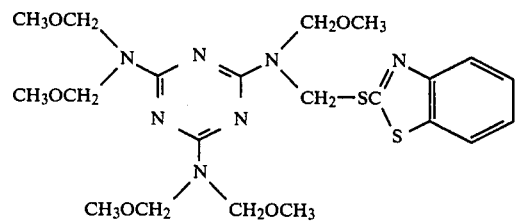

or

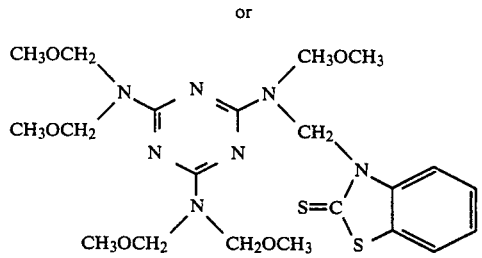

EXAMPLE 3

Wire coat compounds were mixed according to the basic formula shown in Table I. The variations in the adhesion promoter were as follows: phr=parts by weight per 100 parts rubber
Run 1—No adhesion promoter, a control.
Run 2—HMMM at 3 phr.
Run 3—HMMM at 3 phr plus MBT at 0.15 phr.
Run 4—Promoter A at 4 phr.
Run 5—Promoter B at 4 phr.

TABLE I

| Ingredient | phr |
|---|---|
| 1. Cis 1,4-polyisoprene | 100 |
| 2. Carbon black | 57 |
| 3. Antidegradant | 0.75 |
| 4. Stearic acid | 2 |
| 5. Zinc Oxide | 8 |
| 6. Silica | 10 |

TABLE I-continued

| Ingredient | phr |
|---|---|
| 7. Sulfenamide | 0.75 |
| 8. Sulfur | 4 |
| 9. Adhesion Promoter | Variable |

The compounds were mixed as follows: a masterbatch consisting of ingredients 1 through 4 was made in a Banbury, with final mixing carried out on a mill at about 110° C.; the resulting masterbatch was then cooled and ingredients 5 and 6 were added in a Banbury at a temperature of about 70° C.; the balance of the ingredients were added in a mill mix at about 45° C.

The wire cable used in the tests had a 3×0.20+6×0.38 construction and is commonly used in making the plies of a pneumatic tire. The surface of each strand of steel is coated with a brass alloy containing 69% copper and 31±4% zinc at the rate of 6.5±1.5 grams of brass per kilogram of steel.

The wire cable was embedded in the rubber specimens prepared following the method described in U.S. Pat. No. 4,095,465 to Rongone et al, issued June 20, 1978. The specimens were vulcanized at 150° C. for about 25 minutes to about 60 minutes, the optimum cure times having been predetermined by means of a Monsanto oscillating disc rheometer according to ASTM D-2084-79 test method at 150° C. The scorch time, $t_s2$, the optimum cure times, $t_c90$ and the maximum torque, $M_H$ are shown in Table II.

TABLE II

| Run No. | Adhesion Promoter | Time, min $t_s2$ | Time, min $t_c90$ | Torque, N.m $M_H$ |
|---|---|---|---|---|
| 1 | None | 5.5 | 33.5 | 9.2 |
| 2 | HMMM | 6.5 | 60.5 | 10.4 |
| 3 | HMMM and MBT | 5 | 43.5 | 10.8 |
| 4 | Promoter A | 4.5 | 28 | 11.3 |
| 5 | Promoter B | 5.5 | 27 | 11.6 |

The force necessary to pull the adhered cable free from the rubber, the adhesion value in newtons, was determined following the method in Rongone, et al after aging the rubber specimens in water at 90° C. for the lengths of time specified in Table III.

TABLE III

| Run No. | Adhesion Promoter | Adhesion Value, N Days Aging | | | | | |
|---|---|---|---|---|---|---|---|
| | | 0 | 7 | 14 | 28 | 42 | 56 |
| 1 | None | 376 | 404 | 406 | 409 | 392 | 312 |
| 2 | HMMM | 479 | 632 | 607 | 520 | 546 | 494 |
| 3 | HMMM + MBT | 479 | 462 | 476 | 462 | 440 | 420 |
| 4 | Promoter A | 320 | 634 | 643 | 630 | 623 | 536 |
| 5 | Promoter B | 336 | 603 | 587 | 612 | 553 | 425 |

After the determination of the adhesion values, the wires which had been pulled from the test specimens were visually inspected for a relative wire coverage determination. The results are shown in Table IV. The scale of values is from 0 to 10 with 10 being 100% coverage.

TABLE IV

| Run No. | Adhesion Promoter | Relative Wire Coverage Days Aging | | | | | |
|---|---|---|---|---|---|---|---|
| | | 0 | 7 | 14 | 28 | 42 | 56 |
| 1 | None | 7 | 4 | 3 | 5 | 5 | 1 |
| 2 | HMMM | 8 | 10 | 10 | 8 | 9 | 8 |
| 3 | HMMM + MBT | 8 | 6 | 5 | 2 | 3 | 2 |
| 4 | Promoter A | 0 | 10 | 9 | 9 | 9 | 8 |
| 5 | Promoter B | 0 | 9 | 9 | 9 | 8 | 4 |

EXAMPLE 4

In order to compare compounds containing HMMM and MBT at equimolar levels with those containing the HMMM-MBT reaction product of the present invention, compounds were mixed in a Brabender mixer according to the formula of Table I with the following levels of adhesion promoter:

Run 6 None
Run 7 HMMM at 3 phr
Run 8 HMMM at 3 phr plus MBT at 1.25 phr
Run 9 Promoter A at 4 phr The compounds were tested for scorch time, $t_s2$, time to optimum cure, $t_c90$ and maximum torque, $M_H$.

The results are shown in Table V.

TABLE V

| Run No. | Adhesion Promoter | Time, min $t_s2$ | Time, min $t_c90$ | Torque, N.m $M_H$ |
|---|---|---|---|---|
| 6 | None | 5.5 | 33 | 10.2 |
| 7 | HMMM | 5.5 | 47 | 11.9 |
| 8 | HMMM and MBT | 2.5 | 22 | 13.4 |
| 9 | Promoter A | 4 | 29.5 | 12.9 |

While certain representative embodiments and details have been shown for the purpose of illustrating the invention, it will be apparent to those skilled in this art that various changes and modifications may be made therein without departing from the scope of the invention.

What is claimed is:

1. A reaction product of:
   (a) an N-(substituted oxymethyl)melamine and
   (b) a substituted 2-mercaptoarylthiazole accelerator wherein the N-(substituted oxymethyl)melamine has the following structural formula:

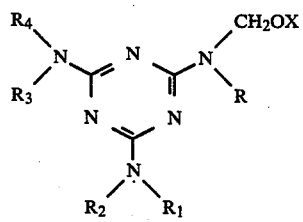

I where X is selected from the group consisting of hydrogen and alkyl radicals having 1 to 8 carbon atoms, R, $R_1$, $R_2$, $R_3$, and $R_4$ are selected from the group consisting of hydrogen, alkyl radicals having 1 to 8 carbon atoms, and —$CH_2OX$ where X is as defined above; and wherein the 2-mercaptoarylthiazole has the following structural formula:

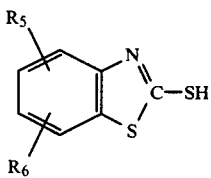

where $R_5$ and $R_6$ are selected from the group consisting of: hydrogen; alkyl radical having from 1 to 8 carbon atoms; alkoxy radicals having from 1 to 4 carbon atoms; phenyl radicals either substituted or unsubstituted; amino radical; nitro radical; hydroxy radical; and halo-radicals.

2. The reaction product according to claim 1 wherein the N-(substituted oxymethyl)melamine is hexakis(methoxymethyl)melamine.

3. The reaction product according to claim 1 wherein the 2-mercaptoarylthiazole is 2-mercaptobenzothiazole.

4. The reaction product according to claim 2 wherein the 2-mercaptoarylthiazole is 2-mercaptobenzothiazole.

5. A compound having the following structural formula:

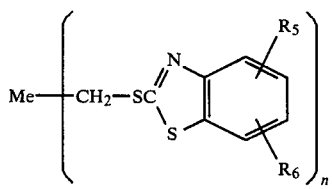

where Me is a melamine structure, n = 1, 2, 3, 4, 5, or 6 and $R_5$ and $R_6$ are selected from the group consisting of: hydrogen; alkyl radicals having 1 to 8 carbon atoms; alkoxy radicals having from 1 to 4 carbon atoms; phenyl radicals either substituted or unsubstituted; amino radical, nitro radical; hydroxy radical; and halo radicals.

6. A process of preparing the compound of claim 5 comprising reacting:
 (a) a N-(substituted oxymethyl)melamine, and
 (b) a substituted 2-mercaptoarylthiazole accelerator wherein the N-(substituted oxymethyl)melamine has the following structural formula:

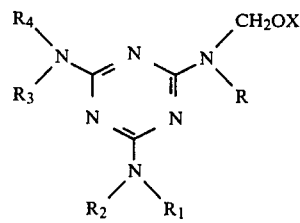

where X is selected from the group consisting of hydrogen and alkyl radicals having 1 to 8 carbon atoms, R, $R_1$, $R_2$, $R_3$, and $R_4$ are selected from the group consisting of hydrogen, alkyl radicals having 1 to 8 carbon atoms, and $-CH_2OX$ where X is as defined above; and wherein the 2-mercaptoarylthiazole has the following structural formula:

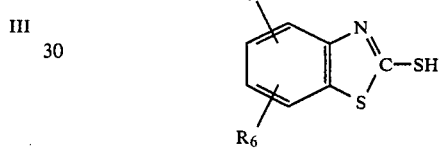

where $R_5$ and $R_6$ are selected from the group consisting of: hydrogen; alkyl radical having from 1 to 8 carbon atoms; alkoxy radicals having from 1 to 4 carbon atoms; phenyl radicals either substituted or unsubstituted; amino radical; nitro radical; hydroxy radical; and halo-radicals.

* * * * *